(12) United States Patent
Morgan

(10) Patent No.: US 6,444,476 B1
(45) Date of Patent: Sep. 3, 2002

(54) LUMINESCENCE ASSAY USING CYCLICAL EXCITATION WAVELENGTH SEQUENCE

(75) Inventor: Christopher Grant Morgan, Irlam (GB)

(73) Assignee: Photonic Research Systems Limited, Salford (GB)

( * ) Notice: Subject to any disclaimer, the term of this patent is extended or adjusted under 35 U.S.C. 154(b) by 0 days.

(21) Appl. No.: 09/701,471

(22) PCT Filed: Jun. 1, 1998

(86) PCT No.: PCT/GB99/01512

§ 371 (c)(1),
(2), (4) Date: Feb. 26, 2001

(87) PCT Pub. No.: WO99/63327

PCT Pub. Date: Dec. 9, 1999

(30) Foreign Application Priority Data

May 29, 1998 (GB) .............................................. 9811483

(51) Int. Cl.[7] .............................................. G01N 21/64
(52) U.S. Cl. ..................................... 436/172; 250/459.1
(58) Field of Search ................................ 436/536, 537, 436/546, 805, 172; 435/6; 422/82.07, 82.08; 250/452.1, 459.1

(56) References Cited

U.S. PATENT DOCUMENTS

| 4,822,733 | A | * | 4/1989 | Morrison | 435/6 |
|---|---|---|---|---|---|
| 5,143,853 | A | * | 9/1992 | Walt | 435/808 |
| 5,246,867 | A | * | 9/1993 | Lakowicz et al. | 422/82.07 |
| 5,498,875 | A | * | 3/1996 | Obremski et al. | 250/458.1 |
| 5,523,210 | A | * | 6/1996 | Paulus | 435/7.91 |
| 5,624,847 | A | * | 4/1997 | Lakowicz et al. | 436/163 |
| 5,656,433 | A | * | 8/1997 | Selvin et al. | 435/6 |
| 5,911,952 | A | * | 6/1999 | Tsuji | 250/458.1 |
| 5,998,146 | A | * | 12/1999 | Latva et al. | 435/6 |
| 6,159,686 | A | * | 12/2000 | Kardos et al. | 250/484.2 |
| 6,245,514 | B1 | * | 6/2001 | Wittwer | 435/6 |
| 6,263,286 | B1 | * | 7/2001 | Gilmanshin et al. | 435/6 |

* cited by examiner

Primary Examiner—Jeffrey Snay
(74) Attorney, Agent, or Firm—Woodard, Emhardt, Naughton, Moriarty & McNett

(57) ABSTRACT

A method for the conduct of a measurement of proximity between luminescent species based on detection of transfer of excitation energy between them. A first photoluminescent species (the "donor") and a second photoluminescent species (the "acceptor") are provided and are such that the donor species and the acceptor species have at least some excitation spectral regions which differ and that at least a part of the emission spectrum of the donor overlaps with at least a part of the excitation spectrum of the acceptor. The donor species is excited with a cyclical temporal sequence of wavelength bands, optionally provided as pulses or modulated in intensity, giving rise to a characteristic temporal fluctuation in emission therefrom and emission in at least one wavelength band characteristic of the acceptor is analyzed to detect the presence of the said characteristic fluctuation or a subcomponent thereof and optionally also to detect a fluctuation characteristic of direct excitation of the acceptor.

17 Claims, 2 Drawing Sheets

LUMINESCENCE ASSAY USING CYCLICAL EXCITATION WAVELENGTH SEQUENCE

FIELD OF INVENTION

This invention describes an improved method to conduct proximity measurements based on the detection of transfer of excitation energy between species labelled with luminescent chromophores.

BACKGROUND

Luminescence techniques (exemplified by, but riot limited to, fluorescence and phosphorescence) are widely used in a variety of analytical applications. There is much interest in using luminescent labels as replacements for radioisotopes in assays and measurements where very high sensitivity is required. Luminescent labels are also used widely in a number of measurements where proximity between labelled species is to be detected. In particular, many binding assays use luminescence energy transfer measurements to detect the formation or breakdown of a bound complex between appropriately labelled species. The most common technique for such assays is based on a system where one component of the complex (the 'donor') is labelled with a photoluminescent label and a second component (the 'acceptor') is labelled with a species (which might or might not be luminescent) having an absorption spectrum which overlaps with the luminescence emission of the first species. When the labelled species approach sufficiently closely a radiationless resonant transfer of energy takes place such that the luminescence of the excited donor species is wholly or partially quenched while the acceptor species is excited. Radiationless transfer of energy of this type is only efficient when the labelled species approach each other within a few nanometres and the most common example, energy transfer between a fluorescent donor and an acceptor, has an efficiency which decreases as the sixth power of the separation between donor and acceptor. Proximity assays based on resonance energy transfer are very well known in the literature and have found commercial applications, Most often the assays are conducted to detect binding between labelled species, either directly (e.g., a hybridisation between oligonucleotides) or mediated by an analyte of interest (e.g. a 'sandwich'immunoassay), though other formats are also used. An / enzyme, for example, might be assayed on the basis of its ability to catalyse formation or breakdown of a covalent linkage between the donor and acceptor, leading to a change in the level of energy transfer between them. There are very many individual combinations of labelled donor and acceptor species bearing recognition ligands such as antibodies, lectins, various peptides, proteins and glycoproteins, nucleic acids, biotin, avidin, and the like. These are used in a variety of formats well known in the art, based for example on detection of binding of a labelled species or on competitive processes where one or more labelled species is displaced by an analyte.

Energy transfer assays frequently are conducted using a luminescent acceptor. detecting the sensitised emission consequent on energy transfer from the donor species. In many cases the assays preferably are conducted in a so-called homogeneous format, where the analyte is introduced into the measurement system and the assay is conducted without physical separation of the bound complex. Homogeneous assays are very convenient, and lend themselves well to automation, but there are potential problems with this approach. There might be coloured materials present in the assay medium which can absorb at the wavelengths of either or both of the donor and acceptor species, or which can quench luminescence from either or both of these by radiationless energy transfer. Equally, there might be other quenching species in the assay medium. The assay medium might be luminescent, as is found in serum samples for example where bilirubin fluorescence is common, and such emission might overlap that of donor and/or acceptor species. These problems are minimised if the sample can be diluted sufficiently to reduce effects due to coloured species and other quenchers, and if the luminescence of the donor and acceptor are distinguishable from that of background. The luminescence assay must be sufficiently sensitive that such dilution does not reduce signal-to-noise ratio to an unacceptable degree.

A further problem with energy transfer assay is common to homogeneous formats and to assays where separation steps can be included. In most assays where sensitised luminescence from the acceptor is measured, there is also some probability of direct excitation of the acceptor by the light used to excite the donor species. This means that the acceptor fluorescence due to energy transfer is detected against a background of directly excited emission which reduces the dynamic range of the assay since small changes above background cannot readily be measured. In additions there might be some level of overlap between the long wavelength 'tail' of the emission from the donor species and the spectral region where acceptor emission is detected.

It is a purpose of the present invention to minimise the effects of these potential difficulties, and to provide adequate sensitivity for assay of diluted samples where necessary.

It is important to understand that sensitivity in the context of luminescence detection is rarely limited by the ability to detect a signal. Photon counting methods are easily able to detect single atoms and molecules of fluorescent substances. It is the ability to reject unwanted background signals that sets the limit of sensitivity for most measurements, and this is a particular problem in homogeneous assay formats where many potentially luminescent species might be present in the assay medium. Consequently, sensitivity is determined by the selectivity of detection. The present invention provides a means to increase selectivity of detection in the context of luminescence energy transfer.

SUMMARY OF INVENTION

The invention describes an improvement in the conduct of a measurement of proximity between luminescent species based on detection of transfer of excitation energy between them wherein a first photoluminescent species (the 'donor') and a second photoluminescent species (the 'acceptor') are provided and are such that the donor species and the acceptor species have at least some excitation spectral regions which differ and that at least a part of the emission spectrum of the donor overlaps with at least a part of the excitation spectrum of the acceptor the donor species is excited with a cyclical temporal sequence of wavelength bands, optionally provided as pulses or modulated in intensity, giving rise to a characteristic temporal fluctuation in emission therefrom and emission in at least one wavelength band characteristic of the acceptor is analysed to detect the presence of the said characteristic fluctuation or a subcomponent thereof and optionally also to detect a fluctuation characteristic of direct excitation of the acceptor.

Further features of the invention are defined in the appended claims.

The invention is useful in assay formats based on radiative or radiationless transfer of excitation energy between a donor and an acceptor species.

DESCRIPTION OF INVENTION (INCLUDING PREFERRED EMBODIMENTS)

Figure 1:
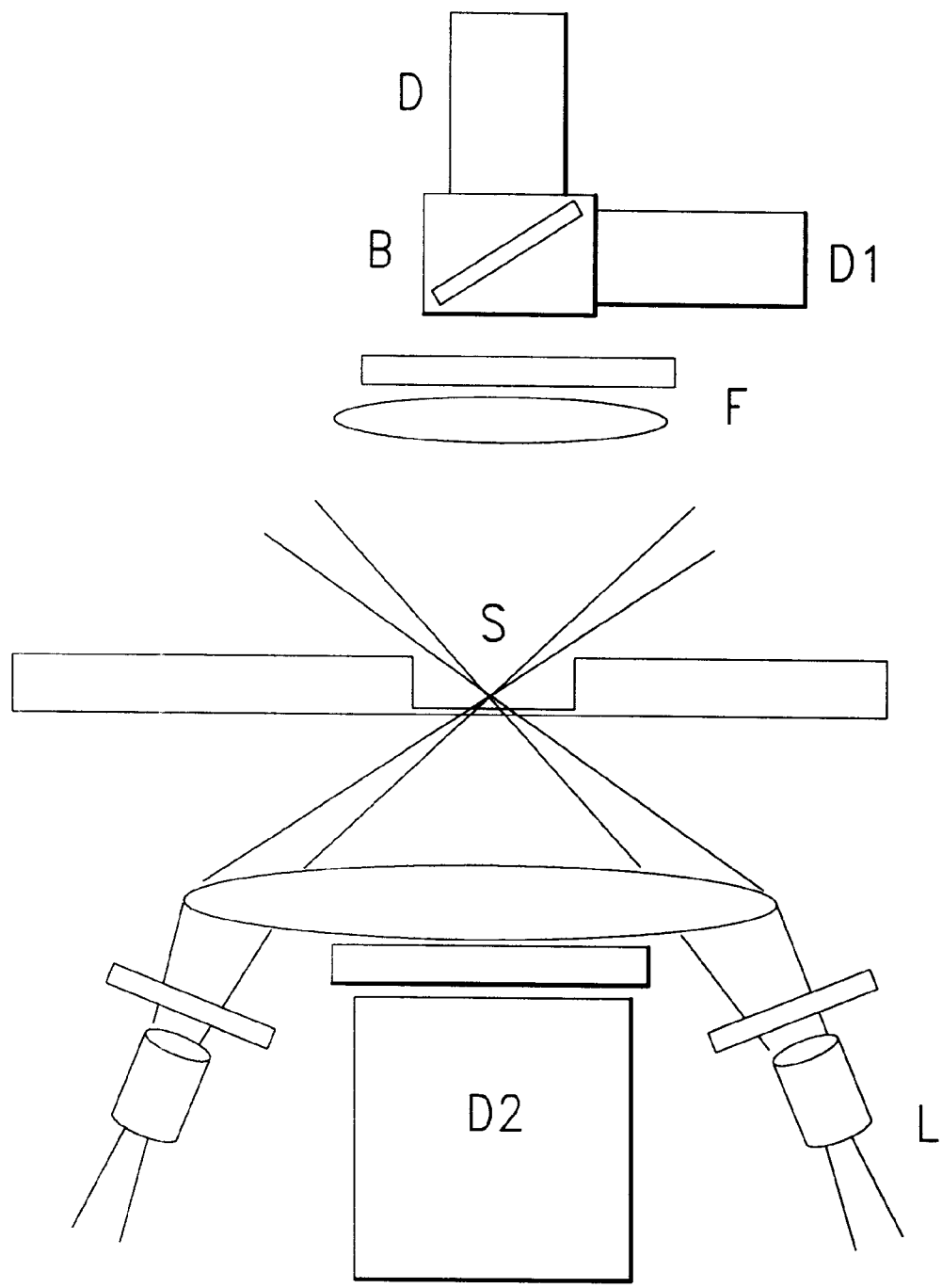
FIG. 1 illustrates one embodiment of apparatus for carrying out the method of the invention.

The invention provides a means to enhance discrimination between emission from the acceptor species which is directly excited by the radiation used primarily to excite the donor and acceptor emission which is sensitised by transfer of energy from the donor. The sensitised emission from the acceptor will have the same temporal signature as tat from the donor whereas the directly excited emission will differ in its temporal fluctuation.

The invention also provides improved rejection of emission from luminescent contaminants in the sample. Detection of a characteristic fluctuation narrows the detection bandwidth relative to unfiltered detection and allows efficient detection of the signals of interest with good rejection of background emission.

The degree of discrimination that can be achieved will depend on the relative bandshapes of the excitation profiles for donor and acceptor species within the wavelength region spanned by the excitation sequence. It will often be advantageous to measure luminescence characteristic of direct excitation of the acceptor species in addition to sensitised luminescence since the former can be used as an internal standard to detect and potentially to correct for effects of coloured materials absorbing emission from the acceptor or other quenching species that might be present in the assay medium. Measurements of characteristic fluctuations can also be made in a spectral region dominated by emission from the donor species to determine the donor emission with suppression of background. This is useful where assays are designed to measure the ratio of donor emission to sensitised emission from acceptor, which is a commonly encountered measurement format.

In practice it will be convenient to analyse the emission fluctuation of donor, acceptor and background individually to determine which temporal frequency components should be used to optimise discrimination. There are many methods to optimise discrimination between temporal signal sequences. For example, an optimum filter can be often be synthesised mathematically or approximated physically according to well known procedures. The transfer function of a filter to separate a first and second signal optimally is given by the ratio of the power spectrum of the first signal to the sum of the power spectra of the first signal and the second signal as described for example in Appendix 5 of 'Electronics for Experimentation and Research' (Brian K. Jones (1986), Prentice Hall International, ISBN 0-13-2507544). It is likely that a simpler approach will suffice in most practical circumstances. For example one or more characteristic fluctuation frequencies might be chosen which are represented strongly in the emission from one of the luminescent species but which are not prominent in the directly-excited emission from other species present in the assay.

The analysis means to detect the desired temporal pattern from the detector might be one or more electronic filters or might use mathematical filtering methods on digitised data from the detector. Alternatively the temporal and/or spectral sensitivity of the detector might be varied synchronously with the excitation sequence to effect detection according to a predetermined correlation scheme. Measurements of a fluctuating signal with a detector sinusoidally-modulated in sensitivity can be used in conjunction with phase-sensitive detection to determine the Fourier component in the signal at the modulation frequency. Alternatively, the detector can be used to perform a cross-correlation analysis if its sensitivity is modulated according to a pattern known to be present in the signal and the result compared with that obtained without such modulation.

The invention can be implemented using the well-known technique of wavelength modulation, which has been used to increase selectivity in analytical detection of fluorophores, but which has not previously been applied to our knowledge to proximity assay. In a wavelength modulation experiment an excitation source is repetitively scanned across the excitation peak of a fluorophore at a fixed frequency F. The emission from the fluorophore will have a temporal component that fluctuates at 2F as a consequence of the increase and decrease of emission for each half cycle as the excitation scans across the peak. Any contaminating fluorophore which has absorbance in the scanned region, but which does not have a peak in this region, will emit fluorescence with little temporal fluctuation at 2F, so that a simple filter tuned to this frequency will increase discrimination against this source of background. The principle can be extended to modulation across the emission peak maximum using a scanning optical filter or monochromator to similar effect. If additional selectivity is required both excitation and emission can be scanned jointly at the same or different frequencies and the resulting fluctuation pattern characteristic of the spectral bandshapes of absorption and emission can be detected by lock-in means at an appropriate frequency or frequencies. The use of modulation in conjunction with a lock-in detection scheme has the advantage of narrowing the measurement bandwidth and allowing measurements to be made in one or more frequency ranges chosen to mininmise external noise contributions.

Wavelength modulation as described is in essence a coding scheme. Luminescence from the species having a given excitation spectrum can be encoded temporally. The presence of the characteristic fluctuation in emission of the acceptor can be detected to distinguish between directly excited emission and sensitised emission mediated by the donor. In its standard form wavelength modulation does not optimise the detected signal however, and in addition to components at 2F much of the signal power will be present in other tonics The method of the invention can be extended to improve on this by controlling the excitation sequence. If the excitation is provided as a sequence of wavelength bands, each of a predetermined intensity, then the programmed sequence can be tailored with knowledge of the excitation spectrum of the target species so that the resultant temporal fluctuation of emission is concentrated in a given harmonic.

The means to provide the excitation sequence of the invention might be a conventional monochromator equipped with a suitable light source. The scanning of the monochromator is preferably controlled electronically, for example under computer control and the intensity of the light source is also preferably capable of programmed control. For example, a pulsed Xenon flashlamp might be used with computer control of the charging conditions to vary the light output in a programmed manner from flash to flash. Conventional optics are rather cumbersome and expensive however. The most preferred means to generate the excitation sequence is to provide a number of light-emitting diodes or other semiconductor sources, each optionally provided with a bandpass filter to transmit a specific wavelength region. The use of light-emitting diodes has several advantages.

- the diodes are physically small and inexpensive
- diodes are available emitting across the spectrum from the near UV to the red
- the operating lifetime of the diodes is very long in normal use
- many types of diode can he pulsed and/or modulated directly at very high speed
- diodes are efficient, easily driven with low cost circuitry and generate little heat
- diodes are easily connected to optical fibres for efficient light delivery or to combine light from a number of diodes.

The invention is useful in assay formats based on radiative or radiationless transfer of excitation energy between a donor and an acceptor species.

In a typical assay based on radiationless transfer of energy a donor species is provided in conjunction with a probe which is capable of binding to a target molecule. The probe might be an antigen or antibody for example, or might be a lectin, oligonucleotide sequence or any other molecule capable of forming a complex with a partner. For the detection of gene sequences by hybridisation an oligonucleotide sequence is commonly used as probe, whereas for many other assays the tight binding between an antibody and an antigen is exploited. In other cases the very stable complex formed between biotin and avidin or streptavidin is used to mediate binding, for example using a biotinylated oligonucleotide to bind to a given gene sequence and adding a fluorescent label conjugated to avidin or streptavidin.

Specific binding interactions are not limited to association between molecules and patterned surfaces of polymer or glass can be prepared having a suitable shape and distribution of functional groups to bind a given molecular species.

A common assay format suited to the invention is the 'sandwich assay' format. An antibody capable of binding to one region of an analyte is labelled with an energy donor species and a second antibody capable of binding to another region of the analyte is labelled with an energy acceptor species. Ternary complexes are formed between the antibodies and the analyte on incubation in the assay medium. Excitation of donor results in efficient transfer of energy to the acceptor species in the complex because of the close proximity between donor and acceptor. In the present invention such energy transfer is detected by exciting the donor species in the manner of the invention, detecting emission from the acceptor species and analysing the detected signal to extract that component having a fluctuation characteristic of donor emission.

Assays based on radiationless transfer of energy are limited to detection of species in close proximity. Resonance energy transfer for example is not easily measured when donor and acceptor are separated by distances greater than 10 nm. For some purposes this is a limitation. In such cases, for example when labels bind at distant sites on a DNA sequence or when an analyte is a large macromolecule and labels bind to regions more thank a few nanometres apart, the invention can be applied using radiative energy transfer. The requirement for radiative energy transfer is merely that a photon emitted by a donor species is absorbed by an acceptor species. This process is most probable when the acceptor species is in close proximity to the emitter and when the acceptor has a high absorbance and a large cross-section. The acceptor is therefore most usefully provided as a highly absorbing particle containing multiple absorbing species. Typically the acceptor species would be a fluorescent particle with a size of the order of microns.

The measurement of radiative energy transfer is similar to that for radiationless energy transfer. Radiationless transfer of energy shortens the emissive lifetime of the donor whereas radiative energy transfer does not affect the donor's lifetime, so that measurements based on the decay time of the donor cannot be used in the latter case. The present invention does not rely on measurements of the lifetime of the donor species and so can be applied equally to assays and measurements of radiative and non-radiative transfer.

The invention is illustrated for example only in FIG. 1 which shows a light source (L) comprising a cluster of light-emitting diodes, each equipped with a bandpass filter. The diodes are shown as placed around the periphery of a lens so as to focus to a common point, though it is to be understood that other optical arrangements including fibre-optic delivery could also be used. The arrangement shown is one example of so-called 'dark-field' illumination, which is sometimes used in optical microscopy to avoid direct light from a source of illumination from reaching the detector. In the present context dark-field illumination is convenient, though not essential, since it is effective in reducing background from optical filters in the detection lightpath. The diodes are each controlled in intensity by a driving unit (not shown) which is in turn controlled by the computer. A computer is not an absolute requirement but is convenient as a control and analysis unit. The computer furnishes a pre-programmed sequence to the driving unit which drives each diode with pulsed and/or modulated waveforms. A sample (S) is positioned at the common focus and is excited by the emission from the diodes. Emission from the sample is detected in a first detection channel (D) comprising an electronic detector such as a photomultiplier or semiconductor detector equipped with a wavelength selection means, shown in the figure as a bandpass filter (F) to isolate emission characteristic of the acceptor species in the sample. Optionally at least one other detection channel is provided (shown as D1) equipped with a wavelength selection means to isolate emission characteristic of the donor species of the sample. Where the second channel is used in addition to the first channel a convenient means to separate signals in the characteristic wavelength regions is to use a beamsplitter (B). A partially silvered mirror or more commonly a dichroic beamsplitter transmitting a first set of wavelengths to the first detection channel and reflecting a second set of wavelengths to the second channel serves this purpose. It should be understood that other optical geometries are also appropriate to the invention. For example a second detection channel can be placed at D2 as shown. Signals from the detection channel(s) are preconditioned by amplification and optionally by electronic filtering before being presented to the data acquisition unit. It should be understood that dedicated electronic signal processing units such as one or more lock-in amplifiers might be used to process signals either alone or in conjunction with the computer.

In the example the emission wavelengths are shown as being selected by bandpass filters. It can be convenient to use instead a programmable wavelength selector to allow further selectivity on the basis of emission spectral bandshape as outlined earlier. This can be achieved by conventional means, using scanning monochromators for example. However it is convenient to use solid state devices that offer compactness, high throughput and programmable transmission efficiency. Liquid crystal tunable filters (such as are available commercially from Displaytech Ltd and Meadowlark Optics Ltd in the USA) can be scanned rapidly and offer wide apertures for efficient light collection. Acousto-optic tunable filters (available commercially from Brimrose in the USA and Gooch and Housego in the UK, for example) can also be used as electronically scanned monochromators.

The invention as so far described provides an efficient means to discriminate between directly-excited and sensitised emission from an energy acceptor, as well as giving enhanced background rejection. A further consideration is the possibility of emission from the donor species being detected in the wavelength region characteristic of the acceptor emission. This is possible, particularly if the acceptor has a small Stokes shift between absorption and emission (as with dyes such as fluorescein and rhodamine for example). If excitation wavelength encoding alone is used, both donor emission and sensitised acceptor emission will have the same characteristic temporal fluctuation and will be indistinguishable on this basis. However if the emission transmission means is scanned in a programmed manner jointly with the excitation means, the fluctuation patterns of the donor and sensitised acceptor emission will in general be distinguishable.

The encoding scheme of the invention can also be used in conjunction with other means to discriminate between donor emission, background emission, directly-excited acceptor emission and sensitised acceptor emission. One such means which has been described in U.S. Pat. No. 4,822,733 uses donor and acceptor labels that differ in luminescence decay time ('lifetime').

If a donor species with a long luminescence lifetime transfers energy to an acceptor species with a short luminescence lifetime, the donor lifetime is decreased but the sensitised emission follows the decay of the donor. By lifetime discrimination the directly-excited and sensitised emissions of the acceptor can be readily distinguished. This principle is used in a commercial range of binding assays marketed by Packard Bioscience where long-lived lanthanide species transfer excitation energy to short-lived phycobiliproteins for example. Although lifetime resolution is effective in discriminating between direct excitation of acceptor and sensitised excitation from the donor, it does not discriminate effectively against other sources of long-lived emission that arise from contaminants in the assay medium. Other sources of long-lived luminescence are phosphorescence from microplates used in many assay protocol and luminescence emission from optical filters. Thus the method of the present invention can advantageously be combined with lifetime resolution to minimise these sources of background. For efficient operation it is necessary for lifetimes of species to be distinguished to differ appreciably, and in practice at least by a factor of three or very preferably more. If the encoding scheme uses a tunable emission filter to induce characteristic fluctuations dependent on the emission bandshape of the labels, it is also possible to minimise contributions from unwanted long-lived donor emission 'leaking' into the acceptor spectral emission band.

Suitable long-lived donor species amenable to wavelength encoding are complexes of ruthenium with ligands such as bipyridine and bathophenanthroline. These are excited with blue light and can transfer energy to dyes absorbing near 600 nm and emitting further in the red such as phycobiliproteins. It is desirable to use labels which can be excited efficiently by light of wavelength longer than c. 380 nm since this is close to the present short wavelength limit of emission from light-emitting diodes.

An alternative means to implement an assay using lifetime resolution was disclosed in U.S. Pat. No. 4,822,733, but has not found widespread use. This is a format where the donor species is short lived while the acceptor has a longer fluorescence lifetime. As described, this approach suffers from the serious disadvantage that directly-excited acceptor luminescence is indistinguishable from that sensitised by the donor, since both are long-lived. It does allow efficient rejection of scattered light and short-lived background emission however. There is a further advantage that a large number of potential donors are known as short-lifetime species but there are fewer long-lived labels suitable for use as energy donors. As an example, a variety of types of labelled microsphere are suitable for use as energy acceptors and binding of small molecules to such microspheres can readily be detected by energy transfer to the multiple absorbing species of the particle. The supporting matrix minimises quenching and allows many dyes to give long-lived emission. However such labels are inefficient as energy donors to small molecules unless the particles are extremely small.

The present invention overcomes the difficulty inherent in the use of a long-lived acceptor with a short lived donor, Both the directly-excited and sensitised luminescence from the acceptor will be long-lived, but the excitation-wavelength encoding process will allow these contributions to be distinguished. As examples of suitable energy transfer pairs, dyes such as fluorescein can transfer to long-lived labels such as eosin or phthalocyanines bound to polymer particles or in glassy matrices. Blue-green emitting dyes such as coumarins excited in the blue, violet and near ultra-violet regions could be used to transfer to long-lived metal complexes such as ruthenium bipyridyl complexes. In these cases the directly excited emission serves as an internal standard to detect quenching of the lone-lived emitter.

The combination of fluorescence lifetime discrimination with an encoded wavelength sequence for excitation and/or emission is also potentially valuable as a means to reduce background in the detection of fluorescent labels where energy transfer is not under investigation. For example and not limitation, the label ethidium bromide binds to DNA and its fluorescence lifetime and absorption maximum both differ between bound and free forms of the dye. Both of these effects can be combined to allow selective detection of bound dye with rejection of background fluorescence from free dye and from other fluorescent materials in the sample. This increase in selectivity increases signal-to-noise ratio and hence improves detection sensitivity for DNA and related molecules using the dye.

Fluorescence lifetime discrimination can be combined with excitation temporal coding in a number of ways. One approach uses light-emitting diodes as the excitation source. Many of these diodes are capable of use in a pulsed mode with pulse widths down to nanoseconds, and can also be modulated in intensity at very high speed. An array of such diodes, each equipped with filters to isolate a given wavelength band and chosen to cover an appropriate spectral range, forms a very appropriate excitation source for the present invention. It is straightforward to drive the diodes in a preprogrammed sequence with fast or slow pulses or to drive the diodes with continuous waveforms such as sinusoids. It can be convenient to link such diodes to optical fibres which can be combined into a bundle, for example as randomised mixtures of fibres from each diode, to facilitate use with other optical systems. In some applications, particularly where it is required to generate UV light and where high pulsed currents are required, it can be necessary to coot the diode structures, and this is conveniently achieved by the use of thermoelectric coolers based on the Peltier effect.

Figure 2:
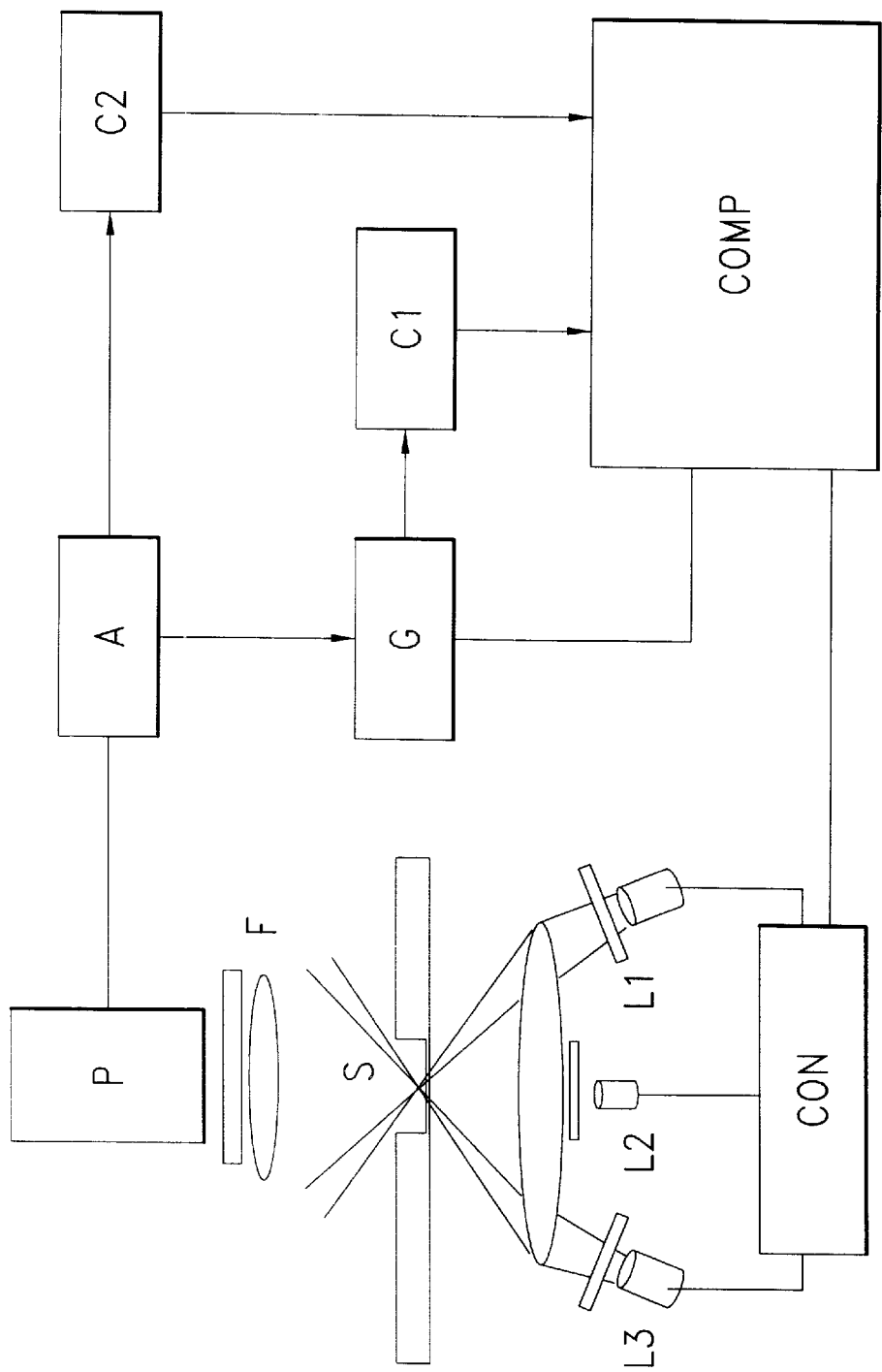
FIG. 2 illustrates a further embodiment of apparatus for carrying out the method of the invention.

An example where lifetime resolution is combined with spectral encoding is given in FIG. 2. This describes a system where several light-emitting diodes (shown in the Figure as three diodes (L)), each equipped with optical filters to isolate a different range of excitation wavelengths are used to illuminate a common region of a sample (S) containing donor and acceptor species differing in lifetime of luminescence which is viewed by a photomultiplier (P) equipped with an optical filter (F) to isolate the emission from a component of interest in the sample. The diodes are energised in sequence giving rise to characteristic fluctuations in emission from the sample component, and the pulse duration and intensity from each diode is determined by the control unit (CON). The signal from the detector is amplified in a fast amplifier (A), the output of which passes to a gating unit (G) with a predetermined delay and gate width, and the output of this unit is fed to a signal processing unit (C1). The output of amplifier (A) also passes directly into a similar signal processing unit (C2). These units comprise programmable filters or correlators able to isolate frequency components characteristic of the temporal fluctuation in emission due to the sequence of excitation wavelengths illuminating the sample. The control unit driving the diodes is programmed via a computer (COMP) which also serves to control the detector delay and gating unit (G) and the processing units (C1) and (C2). The output signal from unit (C1) corresponds to long-lived emission from the sample that also has the temporal fluctuation detected by (C1), while that from (C2) is sensitive to prompt emission in addition to longer-lived emission. It should be clear that the example can be varied and extended in a variety of ways and serves only to illustrate the operation of the invention.

Some light emitting diodes have a spectral emission which varies in response to temperature and/or to drive current. Such diodes can be used for the present invention by providing them with programmed changes in temperature and/or with programmed sequences of drive current of varying intensity and duration. The wavelength encoding is thus implemented by the sequence in which the diodes are driven, while the fast lifetime resolution is implemented by gated detection or by frequency domain methods well known in the art. As an alternative the excitation source might provide two or more wavelengths simultaneously, each coded with a distinguishable temporal sequence of intensity.

Light-emitting diodes presently available are not able to generate wavelengths much below 380 nm efficiently and an alternative approach is required to implement short wavelength excitation. One approach is to use a set of deuterium light sources. These are very stable and generate a continuous spectrum of light down to below 200 nm. Deuterium sources can be modulated at radio frequency and can be pulsed at high speed. We have described the use of deuterium sources for fluorescence lifetime measurement in 'A compact frequency-domain fluorometer with a directly-modulated deuterium light source', by C. G. Morgan, Y. Hua, A. C. Mitchell, J. G. Murray and A. D. Boardman, (Review of Scientific Instruments vol. 67, no.1, pages 41–47, (1996)) and in a related patent FP-A-0 519 930. Although the deuterium source is particularly suited to the present invention where short wavelength excitation is required, it should be apparent that other discharge sources might also be used. For example, mercury vapour can be excited to give pulses of ultra-violet light though the minimum pulse width is longer than for a deuterium source because of the nature of the electronic transitions concerned. Xenon sources can generate short pulses of visible and UV light and a commercial Xenon flashlamp from IBH Ltd in the UK can provide pulse widths as low as 100 ns, though with a small percentage of longer-lived afterglow. Hydrogen discharges are capable of very fast pulsed operation, but are less intense than deuterium sources operated under similar conditions. Many other elements can be included in discharge tubes, and give rise to characteristic emissions that can be used for excitation in the present invention.

For the present invention it is convenient to drive a number of optically filtered sources each with fast pulses or alternatively to code each source with a different frequency or set of frequencies so that their contributions to the excitation process can be decoded subsequently.

As an alternative to single-photon excitation, it is known that many luminescent materials can be excited by simultaneous or sequential absorption of several long wavelength photons to achieve an excited state of higher energy than that of any individual photon used for excitation. This process could also be used in the present invention. In this case the detected pattern is that due to the variation of two-photon or multiphoton excitation cross-section across the absorption band of the donor as different wavelengths or combinations of Wavelength are provided in sequence to match energy levels across the single-photon absorption band. This is to be distinguished from schemes where multiphoton excitation is limited to a particular combination of wavelengths and is not associated with exploitation of spectral variations of donor cross-section for temporal coding. Examples of multiphoton excitation of fluorophores are given in EP-A-0 666 473 and U.S. Pat. No. 5,034,613 and labels suitable for multiphoton excitation are discussed in WO-A-94/07142 (PCT/US93/08712) and in our co-pending patent application WO-A-99/43072 (PCT/GB98100/769). Suitable labels are commonly particles or crystals containing a number of emissive species within the protective matrix, and often in conjunction with sensitising agents that can transfer energy to the emissive species. For example upconversion phosphors are known based on ytterbium ion as sensitiser transferring energy by a multistep process to luminescent lanthanide ions such as erbium and thulium. Upconversion is efficient for ions in a matrix characterised by a low phonon energy to minimise radiationless deactivation of the excited species.

The detectors for the present invention can be of any type, but the invention is well suited to use with imaging detectors such as CCD arrays, intensified imaging detectors and the like. Some versions of such detectors can also be gated or modulated to implement lifetime-resolved detection with nanosecond resolution or better. For example, image intensifiers can be used in this way as described in our patent EP-A-0 519 930, while interline CCD cameras can be electronically shuttered or can be used in a modulated form. Modulated CCD imagers suitable for lifetime-resolved imaging in the microsecond time range are available commercially from Photonic Research Systems Ltd in the UK. Electronic shuttering of CCDs has also been investigated by this company and time resolution of a few nanoseconds has been achieved.

Imaging detectors offer the possibility of making large numbers of measurements in parallel and are well suited to assay procedures such as high-throughput drug screening and other areas where the present invention finds application. Imaging detection as outlined also offers the means to combine lifetime resolution with spectral encoding schemes of the present invention for simultaneous measurements on several samples and this is an important advantage.

Imaging detectors can be used with coded excitation sequences, either decoding the signal by serially processing a sequence of images, or else by interposing an optical modulator such as a controllable light valve or attenuator between the sample and the detector. Alternatively, in some cases the sensitivity of the detector can be modulated directly as described above, There are also available options for decoding a signal based on the emission spectral bandshape, for example using an imaging acousto-optic tunable filter, electrically-tunable liquid-crystal wavelength filter or tunable Fabry-Perot cavity. Interference filters can also be used as tunable elements if they are tilted from the optical axis. Other filters have been described in the literature and may be suitable for the purposes of the invention. For example a so-called Christiansen filter can be implemented by dispersing particles of one medium in a second medium of different refractive index, where the refractive index of one component varies markedly with wavelength and that of the other medium varies with temperature. The filter is tuned by variation in temperature and transmits light at a wavelength where the refractive index of the medium matches that of the dispersed phase. Variants on the principle can be considered where the refractive index of one of the components can be tuned electrically (e.g. a liquid crystal) or via pressure variation.

What is claimed is:

1. A method of effecting measurement of proximity between luminescent species based on detection of transfer of excitation energy therebetween, the method comprising providing a first photoluminescent species (the 'donor') and a second photoluminescent species (the 'acceptor') which are such that the donor species and the acceptor species have at least some excitation spectral regions which differ and also such that at least a part of the emission spectrum of the donor overlaps with at least a part of the excitation spectrum of the acceptor, exciting the donor species with an excitation source, and analyzing emission of the acceptor using a detection means, characterized in that the donor species is excited with a cyclical temporal sequence of wavelength bands, optionally provided as pulses or modulated in intensity, giving rise to a characteristic temporal fluctuation in emission from the donor species, and emission in at least one wavelength band characteristic of the acceptor is analyzed to detect the presence of the said characteristic fluctuation or a subcomponent thereof and optionally also to detect a fluctuation characteristic of direct excitation of the acceptor.

2. A method according to claim 1 wherein luminescence is also measured in a spectral region characteristic of donor emission and a temporal fluctuation characteristic of the donor is detected.

3. A method according to claim 1 wherein excitation wavelengths are scanned cyclically in a continuous or discrete manner across the excitation maximum of the donor at a first scanning frequency and luminescence is detected at one temporal frequency or more that is an integral multiple of the said scanning frequency.

4. A method according to claim 3 wherein the excitation wavelengths are each programmed in intensity so as to concentrate detected signal in a given harmonic of the cyclic scanning frequency.

5. A method according to claim 1 wherein the excitation source is a plurality of light-emitting diodes, operated individually or in groups in a programmed sequence and with a programmed intensity.

6. A method according to claim 1 wherein the excitation source comprises a plurality of light sources coupled to a fibre-optic light guide or liquid light guide.

7. A method according to claim 6 wherein the light sources are based on plasma emission from excited hydrogen, deuterium, mercury, xenon or other element.

8. A method according to claim 1 wherein the excitation source illuminates a sample in a 'dark-field' configuration such that the sample is excited obliquely or with a hollow cone of light illuminating a given region in space and wherein the said region is viewed by one or more detection means at an angle or angles chosen to minimize direct exposure of the said detection means to the exciting radiation.

9. A method according to claim 1 wherein the detection means is equipped with a tunable wavelength-selective filter and this is scanned cyclically across at least a part of the emission band of the acceptor species giving rise to a characteristic temporal fluctuation in detected signal therefrom, and the superposition of the said fluctuation and that due to the cyclic variation of excitation wavelength is measured to detect the joint fluctuation or characteristic temporal components thereof.

10. A method according to claim 1 wherein the detection means is equipped with a tunable optical filter comprising or containing a liquid-crystalline medium, an acousto-optic tunable filter, a tunable Fabry-Perot cavity filter, an interference filter tuned by tilting from the optical axis or a filter based on wavelength-dependent scattering from particles in a medium, such as a Christiansen filter.

11. A method according to claim 1 wherein the detection means is an imaging detector.

12. A method according to claim 11 wherein the detection means can be gated or modulated in sensitivity and where such gating or modulation is used to facilitate selective detection of emission from one or more of the donor and acceptor.

13. A method according to claim 1 wherein the excitation of the donor species is by simultaneous or sequential absorption of two or more photons of the same or different wavelength.

14. A method according to claim 13 wherein the donor species is an upconversion medium based on direct or sensitized excitation of emissive species within a supporting matrix.

15. A method according to any preceding claim wherein the excitation means is driven to produce pulsed or modulated light and a measurement is made by time-domain or frequency-domain methods to detect a signal jointly on the basis of the emissive lifetime of one or more of the donor and acceptor and of the temporal fluctuations in detected emission resulting from either or both of the cyclic variation of excitation wavelength and the cyclic variation of optical wavelengths passed to the detector.

16. A method according to claim 15 wherein the donor has an emissive lifetime at least threefold longer than that of the acceptor.

17. A method according to claim 15 wherein the acceptor has an emissive lifetime at least threefold longer than the donor.

* * * * *